United States Patent
Park et al.

(10) Patent No.: US 7,332,274 B2
(45) Date of Patent: Feb. 19, 2008

(54) PROCESS OF QUALITY EXAMINING FOR MICROARRAY OF BIOLOGICAL MATERIAL

(75) Inventors: Han-Oh Park, Daejon (KR); Jin-Tae Jeon, Daejon (KR); Gui-Hwan Oh, Daejon (KR); Jae-don Lee, Daejon (KR)

(73) Assignee: Bioneer Corporation, Daejon (KR)

( * ) Notice: Subject to any disclaimer, the term of this patent is extended or adjusted under 35 U.S.C. 154(b) by 301 days.

(21) Appl. No.: 10/180,961

(22) Filed: Jun. 27, 2002

(65) Prior Publication Data
US 2003/0032040 A1 Feb. 13, 2003

(30) Foreign Application Priority Data
Jun. 28, 2001 (KR) ................. 2001-37819

(51) Int. Cl.
C12Q 1/68 (2006.01)
C12M 1/34 (2006.01)
C12M 3/00 (2006.01)
G01N 33/543 (2006.01)
G01N 33/551 (2006.01)
G01N 21/00 (2006.01)
G01N 21/75 (2006.01)
G01N 33/53 (2006.01)

(52) U.S. Cl. ............... 435/6; 435/287.1; 435/287.2; 435/288.3; 436/518; 436/524; 436/164; 436/800; 436/809

(58) Field of Classification Search ............ None
See application file for complete search history.

(56) References Cited

U.S. PATENT DOCUMENTS 5,324,633 A 6/1994 Fodor et al.
5,677,197 A * 10/1997 Gordon et al. ............ 436/518
5,843,655 A 12/1998 McGall
6,245,518 B1 * 6/2001 Baier ........................... 435/6

FOREIGN PATENT DOCUMENTS

WO WO 99/39817 8/1999
WO WO 02/18655 3/2002

OTHER PUBLICATIONS

Shearstone, J. R. et al., "Nondestructive Quality Control for Microarray Production", Biotechniques, vol. 32, pp. 1051, 1052, 1054, 1056, 1057 (May 2002).*
Haugland, R.P., "Handbook of Fluorescent Probes and Research Chemicals", Sixth Edition, Molecular Probes, pp. 8-46 (1996).*
Hegde, P., et al., "A Concise Guide to cDNA Microarray Analysis," BioTechniques, vol. 29, No. 3, pp. 548-562 (Sep. 2000).

* cited by examiner

Primary Examiner—Teresa E. Strzelecka
(74) Attorney, Agent, or Firm—Gary M. Nath; Tanya E. Harkins

(57) ABSTRACT

The present invention relates a process of quality examining for microarray of biological material. More particularly, the present invention is directed to a process of quality examining for microarray of biological material, which comprises 1) a step for mixing probe and a compound which emits light or heat and does not react with said probe, 2) a step for microarraying the mixture obtained in step 1) on a substrate, and 3) a step for measuring light or heat emitted by the scanning of each spots of the microarray mixture.

11 Claims, 6 Drawing Sheets a) after spotting b) after hybridization

PROCESS OF QUALITY EXAMINING FOR MICROARRAY OF BIOLOGICAL MATERIAL

TECHNICAL FIELD

The present invention relates a process of quality examining for microarray of biological material. More particularly, the present invention is directed to a process of quality examining for microarray of biological material, which comprises a step for mixing probe and a compound which emits light or heat and does not react with said probe, a step for microarraying the mixture obtained in step 1) on a substrate, and a step for measuring light or heat emitted by the scanning of each spots of the microarray mixture.

BACKGROUND ART

A microarray of biological material means a device for detecting genes or proteins wherein a large number of fragments of DNA, RNA or protein, are immobilized on a small substrate in high density. Such microarray chip is applied to researches for analyzing DNA mutations, RNA expressions and functions of proteins for understanding function of genes in large scale.

The microarray of a biological material (hereinafter, Bio-chip) may be classified into cDNA chip, oligonucleotide chip and protein chip on the basis of size of biological materials immobilized thereon. Full-length open leading frames or expressed sequence tag(EST)s having more than five (5) hundred base pairs can be immobilized on the cDNA chip. Oligonucleotides consisting of approximately 15 to 25 base pairs can be immobilized on the oligonucleotide chip.

The biochip on which plasmid DNA probe, oligonucleotide probe or protein is immobilized is primarily used for detecting gene expression, protein activity and DNA mutation. The most general applications of DNA chip, are for observing the difference of RNA expression between normal cell and abnormal cell. For example, researches for analyzing the difference of RNA expression between human normal cell and cancer cell are performed. Various studies employing high-density oligonucleotide chips, have been performed to analyze the type and system of gene expression of *Saccharomyces cerevisea* of which total six (6) thousand genes had been fully discovered.

Meanwhile, probes microarrayed on the biochip, are plasmid DNA comprising cDNA, products of polymerase chain reaction or synthetic oligonucleotide.

Probes can be microarrayed on the substrate through photolithography (Affymetrix Inc.), non-contact printing method using Ink-Jet injection process (Piezoelectric printing; Packard Instrument Inc., Syringe-solenoid printing; Cartesian Techonologies), contact printing method (Quill and Splite Pin; Telechem International Inc., Pin and Ring; Genetic Microsystem, Capillary pin; Bioneer Corp.) and so on.

However, whatever microarraying method is used, the amount of probes arrayed in each spot or in each biochip cannot be uniform and also the feature of spot microarrays can not be regular due to the effects caused from types of slide glass, electric noise generated in measuring wavelength and evaporation of spot.

More specifically, the direct synthesis of oligo-type probes on the substrate through photolithography process has critical problem that oligomers thus prepared on the substrate directly are not homogeneous even in same spot due to the failure of synthetic reaction.

Further, the fluctuation of the amount and feature of microarrayed probes may cause critical error especially in interpreting results of observing the difference of RNA expression pattern. The uniformity and regularity of microarrayed probes also should be secured in case of a biochip used for detecting DNA mutation accurately.

Furthermore, the control of the above uniformity and regularity are very important for the research on that DNA mutation or RNA expression should be observed continuously through same probes by using several biochips.

Therefore, the step for controlling the uniformity and regularity of the amount of probes should be necessarily added to a process for manufacturing biochip. In the addition, it is needed to provide the correction factor that indicate such differences between microarrayed for the bio-chip users in order to secure high fidelity of a bio-chip test result through the correction of the hybridization results.

Therefore, the primary object of the present invention is to provide a process of quality examining for microarray of biological material, which comprises a step for mixing probe and a compound which emits light or heat and does not react with said probe, a step for microarraying the mixture obtained in step 1) on a substrate, and a step for measuring light or heat emitted by the scanning of each spots of the microarray mixture.

The other object of the present invention is to provide a microarray of biological material wherein a mixture of probes and a compound which emits light or heat and does not react with said probe, is micrroarryed on substrate.

DISCLOSURE OF THE INVENTION

The object of the present invention is achieved by providing a process of quality examining for microarray of biological material, which comprises:
1) a step for mixing probe and a compound which emits light or heat and does not react with said probe;
2) a step for microarraying the mixture obtained in step 1) on a substrate; and
3) a step for measuring light or heat emitted by the scanning of each spots of the microarray mixture.

In addition, the above method of the present invention may further comprise a step 4) for calibrating the intensity of light or heat emitted from the hybridized microarray of biological material by using the intensity of light or heat measured in said step 3).

Bio-chip users of the present invention can further perform a step for measuring the intensity of light or heat emitted from hybridization of microarrayed probe and target and a step for calculating a correction factor by using the above-measured intensity of light or heat to exclude error caused by discrepancy between size of each spots, in order to get more accurate experimental results.

The other object of the present invention is to provide a microarray of biological material wherein a mixture of probes and a compound which emits light or heat and does not react with said probe is micrroarryed on substrate.

Probes of the present invention are selected from the group consisting of biological materials formed by linear or circular combinations of peptides including amino acid, nucleic acid, polysaccharide and phospholipid, respectively.

In addition, A compound of the present invention which emits light or heat and does not react with the probe is preferably selected from the group consisting of fluorescent material, chemi-luminescent material, bio-luminescent material, calorimetric material and light-scattering material, and is preferably selected from the group consisting of rhodamine derivatives and fluoresceine derivatives including Fluorescein, Coumarin, 4',5'-Dichloro-2',7'-dimethoxy-fluorescein, Tetramethylrhodamine, X-rhodamine, Eosin, Oregon Green, Rhodamine Green, Rhodamine Red, Texas Red and Rodamine and so on, especially in the case that the biological material is nucleic acid.

Two types of rhodamine (6-carboxyrhodamine 6G; 6-CR6G, 5-carboxyrhodamine 6G; 5-CR6G) of the present invention having following structures is activated in 520 nm and emit fluorescence of which wave length is 545 nm.

In addition, the rhodamines do not react with DNA, RNA and protein, and may be washed easily by water or other aqueous solution after measuring the uniformity of microarray of biological material. Therefore, the rhodamines have the advantages that general chip scanner may be used without any extra equipment and subsequent processs including hybridization is not affected thereby.

<Structural Formulas>

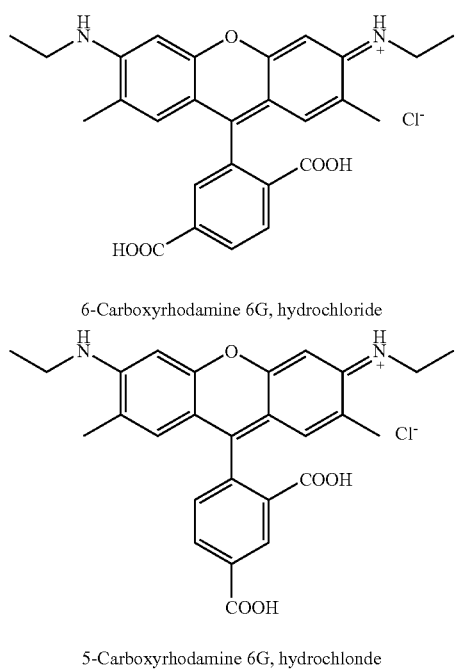

6-Carboxyrhodamine 6G, hydrochloride

5-Carboxyrhodamine 6G, hydrochloride

FIG. 1 shows a process of quality examining for microarray of biological material by using rhodamine 6G.

More particularly, the predetermined amount of rhodamine is mixed with the predetermined amount of probe, and the mixture is microarrayed. The microarray of the mixture is examined the uniformity of each spot through measuring the intensity of fluorescence, and the result of examination is expressed numerically.

Finally, bio-chip users are provided the numerical data along with a biological chip in order to interpret the result more accurately, in DNA chip research.

BRIEF DESCRIPTION OF THE DRAWINGS

The above objects and other advantages of the present invention will become more apparent by describing in detail a preferred embodiment thereof with reference to the attached drawings, in which.

BEST MODE FOR CARRYING OUT THE INVENTION

Hereinafter, the present invention will be described in greater detail with reference to the following examples. The examples are given for illustration of the invention and not intended to be limiting the present invention.

EXAMPLE 1

Determining the Proper Concentration of Rhodamine 6G for the Purpose of Quality Examining for Microarray of Biological Material A rhodamine used for obtaining the data to exclude error caused by discrepancy between size of each spot, should meet the following conditions.

First, the concentration of rhodamine should be in the range which can be detected by scanner. That is, the concentration of rhodamine should not too low to be detected and too high not to be saturated.

Second, the rhodamine of the present invention should have the concentration in which rhodamine can be washed easily, with meeting the above condition.

Third, the rhodamine of the present invention should have the concentration in which subsequent process after washing including hybridazation is not affected.

Therefore, the following embodiment was performed in order to determine the most appropriate concentration of rhodamine 6G to meet the above three (3) conditions.

A. Preparation of Rhodamine 6G 10 mM rhodamine 6G was dissolved in methylalchol, and 10 μl of the solution was diluted in 990 μl Sodium Borate buffer (pH9.0; SB buffer) so that the concentration could be 100 pmol/μl.

Figure 1:
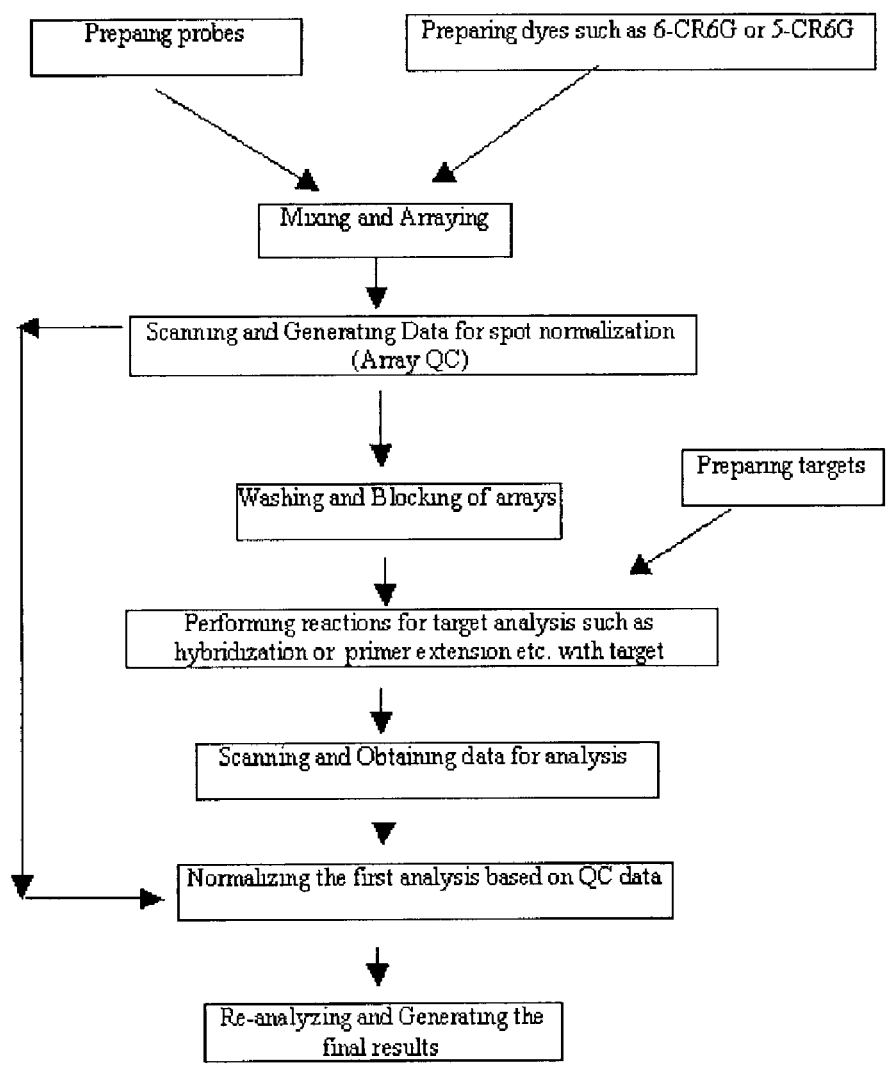
FIG. 1. shows a process which the results of hybridization are normalized in order to secure high quality of a biological chip.
Figure 2:
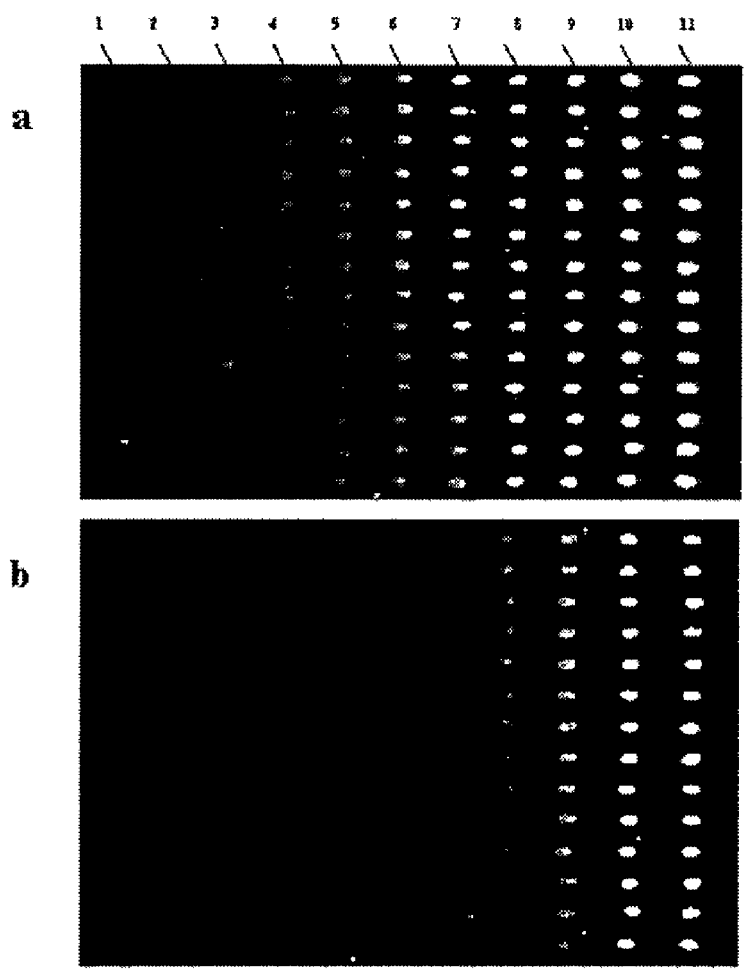
FIG. 2. shows microarrays wherein oligonucleotides are mixed with rhodamine diluted in the predetermined ratio.

100 pmol/μl solution was diluted in SB buffer sequentially, and solutions having eleven (11) kinds of concentration are prepared (see FIG. 2).

B. Microarray of the Mixture of Rhodamine and Oligonucleotide

Each diluted solution was mixed with 10 pmol/μl oligonucleotide. Each mixture was microarrayed on a acrylamide gel pad by using HT-Arrayer™ (Bioneer Corp, Korea) by fourteen times (14), respectively. The gel pad was made through smearing 30 μl of the solution composed of 0.1% glycidyl metacrylate, 8% acrylamide, 1/20 ammonium persulfate and 1/100 N,N,N',N'-tetramethylethylenediamine (TEMED) on a washed slide glass.

C. Scanning and Washing

Rhodamine contained in microarrayed spots was activated in 532nm by using a chip scanner (GenePix4000, Axon Instrument Inc, USA), and was scanned in PMT 600(Photomultipler tubes 600) in order to obtain the fluorescence data.

After that, the chip was washed by water in room temperature for five (5) minutes, and re-scanned in same PMT 600 in same wavelength. The results of scanning were illustrated in FIG. 2.

As illustrated in FIG. 2, 10 pmol/µl oligonuceotide was mixed with rhodamine 6G which was diluted by the predetermined ratio of dilution, and the mixture was microarrayed.

FIG. 2(a) was the result of scanning rhodamine 6G activated in 532 nm, and FIG. 2(b) was the result of scanning in different conditions, for example the condition that a microarray was washed by water in room temperature for five (5) minutes, when increasing the amount of rhodamine which was mixed with oligonucleotide composed thirty (30) monomers.

Rhodamine of which concentration was 1 fmol/µl in lane 1, 5 fmol/µl in lane 2, 10 fmol/µl in lane 3, 50 fmol/µl in lane 4, 100 fmol/µl in lane 5, 500 fmol/µl in lane 6, 1 pmol/µl in lane 7, 5 pmol/µl in lane 8, 10 pmol/µl in lane 9, 50 pmol/µl in lane 10 and 100 pmol/µl in lane 11, was mixed with 10 pmol/µl of oligonucleotide composed of thirty (30) monomers respectively, and each mixture was microarrayed repeatedly fourteen (14) times. The mean diameter of a spot was 180 µm and the mean distance of center to center was 150 µm.

As described in FIG. 2, the intensity of fluorescence was saturated in the case that the concentration of rhodamine was not less than 500 fmol/µl. In addition, the intensity of fluorescence was still detected after washing in the case that the concentration of rhodamine was not less than 1 pmol/µl, because rhodamine was not eliminated through simple washing.

Based on the above results, 100 fmol/µl was selected as the appropriate concentration that the intensity of fluorescence was not saturated and rhodamine was sufficiently eliminated through simple washing for five (5) minutes.

D. Selection of the Washing Condition

It was examined whether 100 fmol/µl rhodamine selected above was eliminated easily by blocking solution (10% ethanolamine) applied generally to a gel pad chip or not.

Figure 3:
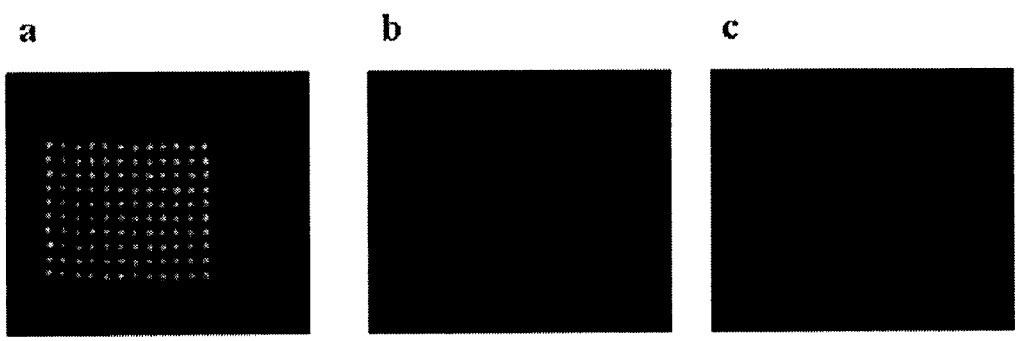
FIG. 3. shows microarrays wherein thirty oligonucleotides (30 mer) are mixed with the same amount of rhodamine.

As illustrated in FIG. 3, 100 fmol/µl rhodamine was mixed with 10 pmol/µl oligonucleotide composed of thirty (30) monomers, and the mixture was microarrayed.

FIG. 3(a) was the results of scanning spots in 532 nm without any treatment after microarraying. FIG. 3(b) was the results of scanning spots in PMT 600 (photomultiplier tubes 600) and FIG. 3(c) was the results of scanning spots in PMT 900 (photomultiplier tubes 900), after washing a microarray by 10% ethanolamine for five (5) minutes.

As results, 100 fmol/µl rhodamine was completely eliminated when washing the microarry by 10% ethanolamine in room temperature for five (5) minutes. That is, no intensity of fluorescence was detected in PMT 600 and in PMT 900. The above results show the advantages of the present invention that an experiment takes less time because a microarry can be washed easily without the addition of extra washing process.

According to the above results, 100 fmol/µl was selected as the most appropriate concentration and washing by water or 10% ethanolamine in room temperature for five (5) minutes was selected as the washing condition.

EXAMPLE 2

The effect of Rhodamine 6G on the Step of Hybridization

Hybridization was performed in order to confirm whether the most appropriate concentration and the washing condition selected in Example 1 were selected properly.

Figure 4:
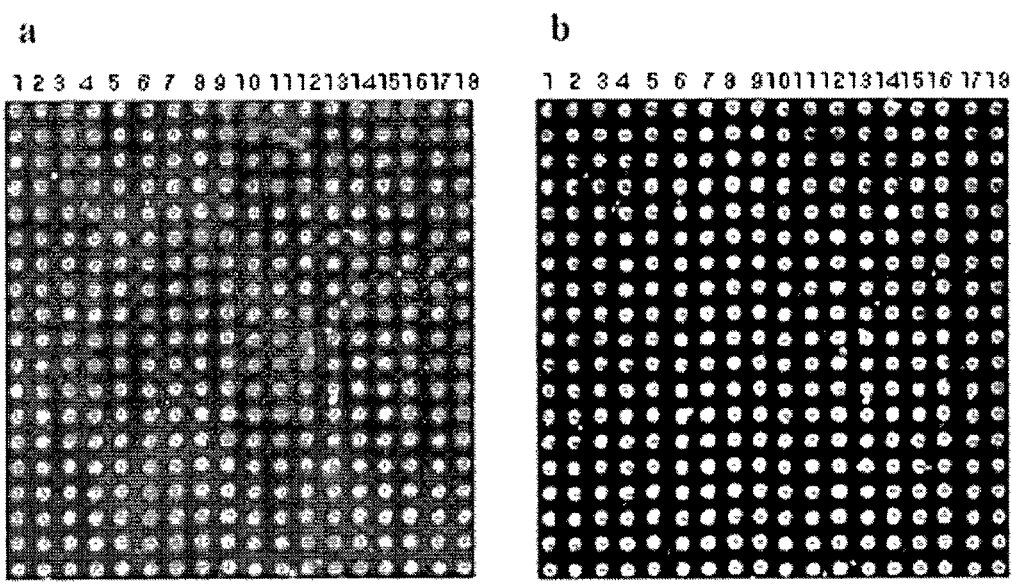
FIG. 4. shows what effect a process for checking the regularity of the amount of probes has on the results of hybridization.

A. Preparation of the Mixture of Rodamine and Oligonucleotide 10 pmol/µl of two types of oligonucleotide was mixed with 100 fmol/µl rhodamine respectively, and the two types of the mixture was mixed with each other sequentially in the ratio from 1:0 to 1.5:8.5 (FIG. 4).

B. Microarray of the Mixture of Rhodamine and Oligonucleotide

Each Mixture was microarrayed on a acrylamide gel pad by using HT-Arrayer™ (Bioneer Corp, Korea) by nineteen (19) times. The gel pad was made through smearing 30 µl of the solution composed of 0.1% glycidyl metacrylate, 8% acrylamide, 1/20 ammonium persulfate and 1/100 N,N,N', N'-tetramethylethylenediamine(TEMED) on a slide glass.

C. Scanning and Washing

Rhodamine contained in microarrayed spots was activated in 532nm by using a chip scanner (GenePix4000, Axon Instrument Inc, USA), and was scanned in PMT 600(Photomultipler tubes 600) in order to obtain the fluorescence data. After that, the chip was washed by 10% ethanolamine in room temperature for five (5) minutes.

D. Hybridization

Two types of microarrayed oligonucleotide were hybridized with each target that was completely complementary to each oligonucleotide and of which 5'-terminal was labeled by cy3 or cy5. The target labeled by 1 pmol fluorescent material was mixed with 20 µl hybridizing buffer (1M NaCl, 1 mM EDTA, 1% Tween 20 and 5 mM sodium phosphate), and reacted with each oligonucleotide in 40° C. for 1 hour. Non-reacted targets and non-specific products of hybridization were eliminated through washing by hybridizing buffer diluted by ten (10) fold in 65° C. for 15 minutes.

E. Scanning

The intensity of fluorescence of hybridization-product was measured by using a chip scanner (GenePix4000, Axon Instrument Inc, USA), after Cy3 was activated in 532 nm and cy5 was activated in 650 nm.

10 pmol/µl of two types of oligonucleotide (comp-cy3 and comp-cy5) was mixed with each other, and the mixture was mixed with 100 pmol/µl rhodamine, and the final mixture was microarrayed (FIG. 4a).

In addition, the microarray was activated in 532nm, and was washed by ethanolamine in room temperature for five (5) minutes. After washing, the above two (2) kinds of oligonucleotide were hybridized with each target oligonucleotide that was completely complementary to each probe and was labeled by cy3 or cy5.

FIG. 4(b) was the result of measuring the intensity of fluorescence after cy3 was activated in 532nm and cy5 was activated in 635 nm. Green color indicates fluorescence resulted from cy3, and red color indicates fluorescence resulted from cy5, and yellow color indicates the mixture of the above two fluorescence. 10 pmol/µl comp-cy3 and 10 pmol/µl comp-cy5 was mixed with each other sequentially in the ratio from 1:0 to 1.5:8.5, and the mixture was microarrayed in lane 1 to lane 18 of FIG. 4 after mixed with 10 pmol/µl rhodamine.

As results, the feature of yellow color indicating the mixture of two colors by fluorescence corresponded with the mixing ratio of two probe-oligonucleotides.

This results showed that rhodamine using for quality examining of microarray of biological material had no effect on a step for hybridization, especially on a step for competitive hybridization which two targets labeled with two kinds of fluorescent material respectively were hybridized in one spot.

That is, the above results show that rhodamine 6G can be used as the material for quality examining for the microarray of biological material because rhodamine does not cause any error in a process for analyzing genes.

EXAMPLE 3

Exclusion of Error Caused by Discrepancy Between Size of Each Spots

This embodiment was performed in order to show a simple example of calculating a correction factor which can exclude error caused by discrepancy between size of each spots. However, the method for calculating a correction factor is not limited to this embodiment.

A. Preparation of the Mixture of Rodamine and Oligonucleotide 100 pmol/µl of one (1) kind of oligonucleotide was mixed with the same amount of 100 fmol/µl rhodamine 6G. The mixture was diluted in SB buffer by two-fold and by four-fold, and each diluted solution was microarrayed three times (FIG. 5a).

Figure 5:
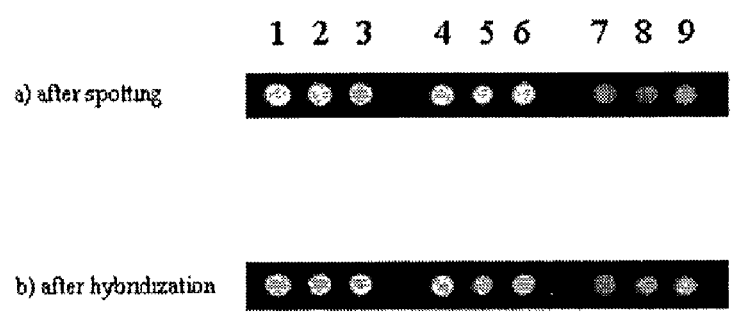
FIG. 5. shows microarrays which are made after mixtures of oligonucleotide and rhodamine are diluted twice by two fold.

The non-diluted solution was microarrayed in lane 1, lane 2 and lane 3 of FIG. 5. The two-fold diluted solution was microarrayed in lane 4, lane 5 and lane 6, and the four-fold diluted solution was microarrayed in lane 7, lane 8 and lane 9.

B. Scanning and Washing

Rhodamine contained in microarrayed spots was activated in 532nm by using a chip scanner (GenePix4000, Axon Instrument Inc, USA), and was scanned in PMT 600(Photomultipler tubes 600) in order to obtain the fluorescence data. After that, the chip was washed by 10% ethanolamine in room temperature for five (5) minutes.

C. Hybridization

The microarrayed oligonucleotide was hybridized with the target that was completely complementary to the oligonucleotide and of which 5'-terminal was labeled by cy3. The target labeled by 1 pmol fluorescent material was mixed with 20 µl hybridizing buffer (1M NaCl, 1 mM EDTA, 1% Tween 20 and 5 mM sodium phosphate), and reacted with the oligonucleotide in 40° C. for 1 hour. Non-reacted targets and non-specific products of hybridization were eliminated through washing by hybridizing buffer diluted by ten (10) fold in 65° C. for 15 minutes.

D. Scanning

The intensity of fluorescence of hybridization-product was measured by using a chip scanner (GenePix4000, Axon Instrument Inc, USA), after Cy3 was activated in 532nm (FIG. 5b). Table 1 shows the mean intensity of fluorescence obtained respectively after microarraying and after hybridization. Each spot had the area of 7850 µm$^2$, and the semi-diameter of 50 µm.

The intensity of fluorescence of rhodamine obtained after microarraying was linearly proportioned to the concentration of microarrayed oligonucleotide (y=541,63x−12861, $R^2$=0.9453). In addition, the intensity of fluorescence of rhodamine obtained after microarraying highly correlated with the intensity of fluorescence of cy3 obtained after hybridization (R=0.9096).

That is, this results shows that the discrepancy between the amount of microarrayed probes has direct effect on the final hybridization result. Therefore, the final users of a biological chip should be provided the date which can exclude error caused by the above discrepancy in order to correct the final hybridization result. Table 1 shows the mean intensity of fluorescence respectively obtained after microarraying and after hybridization for spots in FIG. 5.

Figure 6:
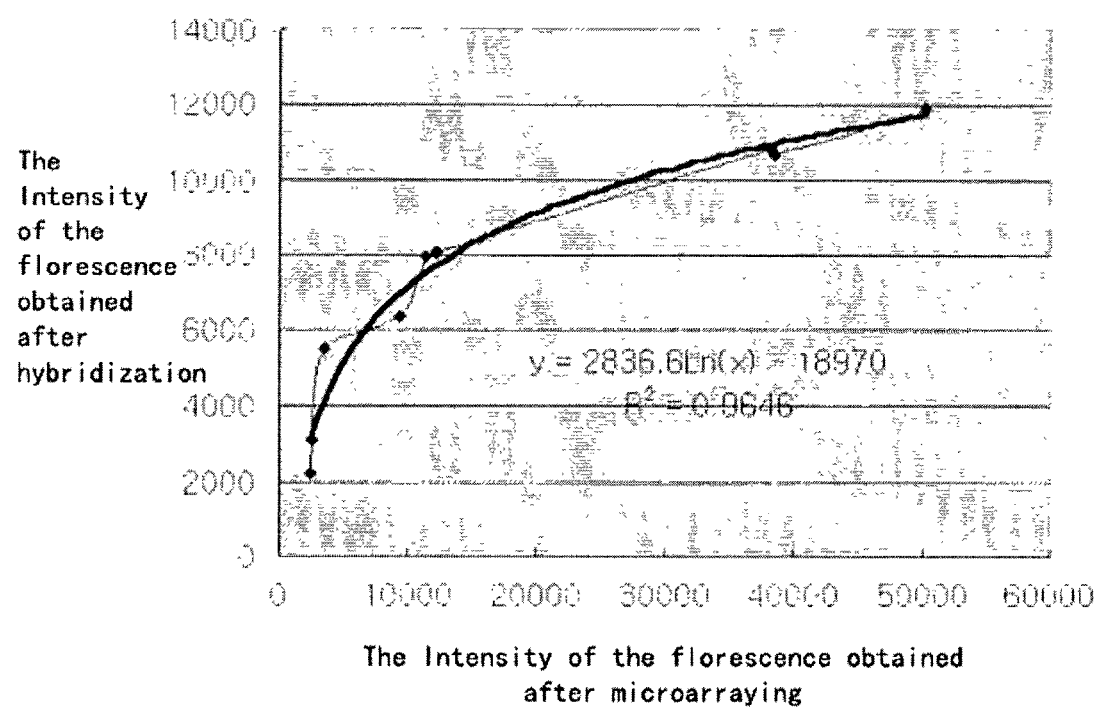
FIG. 6. shows a regressive equation which indicates relationship between fluorescence of microarrays after microarraying and fluorescence of microarrays after hybridization.

FIG. 6 shows the results of calibrating the regressive equation with respect to the relationship between the intensity of the fluorescence obtained after microarraying and the intensity of the fluorescence obtained after hybridization, by using the mean intensity of fluorescence emitted in the area of 7850µm$^2$ after the intensity of fluorescence in each spot was obtained in 532nm.

The regressive equation was Y(the intensity of fluorescence obtained after hybridization)=2836.6Ln(X;the intensity of fluorescence obtained after microarraying)−18970 (R=0.9646).

The intensity of fluorescence of cy3 was inferred from the intensity of fluorescence of rhodamine 6G of which range was 1,000 to 100,000 by using the above regressive equation. The discrepancy between the intensity of fluorescence of rhodamine 6G means the discrepancy between the amount of microarrayed probes, for example oligonucleotide. The intensity of fluorescence of rhodamine 6G of which range was 1,000 to 100,000 can cover almost possible variation thereof.

The arithmetic mean of the intensity values of fluorescence obtained after microarraying was calculated and was converted to the intensity of fluorescence obtained after hybridization (11749.61).

The intensity values of fluorescence obtained after hybridization was subtracted from the value calculated by conversion (11749.61). The values calculated by subtraction were used as correction factors, and the values calculated by adding the correction factor to the actual intensity of fluorescence are always 11749.61.

More particularly, the variation in the amount of probes among spots caused the variation in the intensity of fluorescence of rhodamine, in the case that probes having the predetermined concentration are mixed with 100 fmol/µl rhodamine and the mixture is microarrayed. Finally, the variation in the intensity of fluorescence of rhodamine has the effect on the intensity of fluorescence obtained after hybridization.

For example, assuming that the intensity of fluorescence emitted in spot A is 1000 after microarraying and 1000 after hybridization and the intensity of fluorescence emitted in spot B is 2000 after microarraying and 1500 after hybridization, it can be misunderstood that the amount of hybridized target in spot B is larger than the amount of hybridized target in spot A when judging only by the actual intensity of fluorescence after hybridization.

However, such discrepancy between the intensity of fluorescence can be corrected by subtracting the discrepancy resulting from the amount of microarrayed probes in order to compare the intensity of fluorescence accurately.

In the case that each appropriate correction factor, 11125.07 and 9158.89 is added to each intensity of fluorescence in spot A and in spot B, the intensity of fluorescence is 12125.07 in spot A and 11158.89 in spot B. Therefore, assuming that the same amount of probes is contained in spot A and in spot B, it could be concluded that the amount of hybridized target in spot A is larger than the amount of hybridized target in spot B.

As explained the above, the correction factor can be necessarily used in order to interpret the final results more accurately. Table 2 shows the correction factors calculated by the regressive equation (Y(the intensity of fluorescence obtained after hybridization)=2836.6Ln(X; the intensity of fluorescence obtained after microarraying)−18970).

TABLE 1

The mean intensity of fluorescence according to each concentration of oligonucleotide after hybridization

| No. | the concentration of microarrayed oligonucleotide (pmole/ul) | the mean intensity of fluorescence obtained in 532 nm after microarraying | the mean intensity of fluorescence obtained in 532 nm after hybridization |
|---|---|---|---|
| 1 | 100 | 50308 | 11889 |
| 2 | 100 | 38592 | 10630 |
| 3 | 100 | 38254 | 10848 |
| 4 | 50 | 12190 | 8069 |
| 5 | 50 | 9338 | 6322 |
| 6 | 50 | 11395 | 7952 |
| 7 | 25 | 3576 | 5497 |
| 8 | 25 | 2534 | 3090 |
| 9 | 25 | 2423 | 2232 |

TABLE 2

The correction factors calculated by the regressive equation (Y = 2836.6 Ln(X) − 18970)

| the mean intensity of fluorescence obtained in 532 nm after microarraying | the mean intensity of fluorescence obtained in 532 nm after hybridization | correction factor | the mean normalized intensity of fluorescence obtained in 532 nm after hybridization |
|---|---|---|---|
| 1000 | 624.5386244 | 11125.07138 | 11749.61 |
| 2000 | 2590.719917 | 9158.890083 | 11749.61 |
| 3000 | 3740.862242 | 8008.747758 | 11749.61 |
| 4000 | 4556.901209 | 7192.708791 | 11749.61 |
| 5000 | 5189.870207 | 6559.798798 | 11749.61 |
| 6000 | 5707.048535 | 6042.566465 | 11749.61 |
| 7000 | 6144.307353 | 5605.302647 | 11749.61 |
| 8000 | 6525.082501 | 5226.527499 | 11749.61 |
| 9000 | 6857.18586 | 4892.42414 | 11749.61 |
| 10000 | 7156.051499 | 4593.558501 | 11749.61 |
| 11000 | 7426.408355 | 4323.201645 | 11749.61 |
| 12000 | 7673.224827 | 4076.385173 | 11749.61 |
| 13000 | 7900.273972 | 3849.336028 | 11749.61 |
| 14000 | 8110.488846 | 3639.121354 | 11749.61 |
| 15000 | 8306.193825 | 3443.416175 | 11749.61 |
| 16000 | 8489.263794 | 3280.346206 | 11749.61 |
| 17000 | 8661.231596 | 3088.378404 | 11749.61 |
| 18000 | 8823.367153 | 2926.242847 | 11749.61 |
| 19000 | 8976.734233 | 2772.875767 | 11749.61 |
| 20000 | 9122.232792 | 2627.377208 | 11749.61 |
| 21000 | 9260.630971 | 2488.979029 | 11749.61 |
| 22000 | 9392.589648 | 2357.020352 | 11749.61 |
| 23000 | 9518.681517 | 2230.928483 | 11749.61 |
| 24000 | 9639.40612 | 2110.20388 | 11749.61 |
| 25000 | 9755.201769 | 1994.408211 | 11749.61 |
| 26000 | 9866.455264 | 1883.154736 | 11749.61 |
| 27000 | 9973.509478 | 1776.100522 | 11749.61 |
| 28000 | 10076.66994 | 1672.940062 | 11749.61 |
| 29000 | 10176.20998 | 1573.400024 | 11749.61 |
| 30000 | 10272.37512 | 1477.234883 | 11749.61 |
| 31000 | 10365.38873 | 1384.223271 | 11749.61 |

TABLE 2-continued

The correction factors calculated by the regressive equation (Y = 2836.6 Ln(X) − 18970)

| the mean intensity of fluorescence obtained in 532 nm after microarraying | the mean intensity of fluorescence obtained in 532 nm after hybridization | correction factor | the mean normalized intensity of fluorescence obtained in 532 nm after hybridization |
|---|---|---|---|
| 32000 | 10455.44509 | 1294.164914 | 11749.61 |
| 33000 | 10542.73197 | 1206.878027 | 11749.61 |
| 34000 | 10627.41289 | 1122.197112 | 11749.61 |
| 35000 | 10709.63894 | 1039.971064 | 11749.61 |
| 36000 | 10789.54845 | 960.0615548 | 11749.61 |
| 37000 | 10867.36838 | 882.3416246 | 11749.61 |
| 38000 | 10942.91553 | 806.694475 | 11749.61 |
| 39000 | 11016.59759 | 733.0124102 | 11749.61 |
| 40000 | 11088.41408 | 661.1959161 | 11749.61 |
| 41000 | 11158.45715 | 591.1528512 | 11749.61 |
| 42000 | 11226.81226 | 523.7977364 | 11749.61 |
| 43000 | 11293.55887 | 456.0511275 | 11749.61 |
| 44000 | 11358.77094 | 360.8390601 | 11749.61 |
| 45000 | 11422.51744 | 327.0925572 | 11749.61 |
| 46000 | 11484.86281 | 264.7471904 | 11749.61 |
| 47000 | 11545.86731 | 203.7426886 | 11749.61 |
| 48000 | 11605.58741 | 144.0225881 | 11749.61 |
| 49000 | 11664.07608 | 85.53391802 | 11749.61 |
| 50000 | 11721.38306 | 28.22691844 | 11749.61 |
| 51000 | 11777.55521 | −37.94521415 | 11749.61 |
| 52000 | 11832.63656 | −83.02855649 | 11749.61 |
| 53000 | 11886.66867 | −137.0586663 | 11749.61 |
| 54000 | 11939.69077 | −190.0807708 | 11749.61 |
| 55000 | 11991.73994 | −242.1299376 | 11749.61 |
| 56000 | 12042.85123 | −293.2412303 | 11749.61 |
| 57000 | 12093.05785 | −343.4478507 | 11749.61 |
| 58000 | 12142.39127 | −392.7812681 | 11749.61 |
| 59000 | 12190.88134 | −441.2713877 | 11749.61 |
| 60000 | 12238.55641 | −488.9464096 | 11749.61 |
| 61000 | 12285.44343 | −535.8334275 | 11749.61 |
| 62000 | 12331.56802 | −581.958021 | 11749.61 |
| 63000 | 12376.95459 | −827.3445892 | 11749.61 |
| 64000 | 12421.62638 | −672.0163786 | 11749.61 |
| 65000 | 12465.60555 | −715.9965541 | 11749.61 |
| 66000 | 12508.91327 | −759.3032856 | 11749.61 |
| 67000 | 12551.56971 | −801.9597085 | 11749.61 |
| 68000 | 12593.59418 | −843.9841809 | 11749.61 |
| 69000 | 12635.00514 | −885.3951353 | 11749.61 |
| 70000 | 12675.82023 | −926.210228 | 11749.61 |
| 71000 | 12716.05636 | −953.4463636 | 11749.61 |
| 72000 | 12755.72974 | −1006.119738 | 11749.61 |
| 73000 | 12794.85588 | −1045.245875 | 11749.61 |
| 74000 | 12833.44967 | −1063.839668 | 11749.61 |
| 75000 | 12871.52543 | −1121.915407 | 11749.61 |
| 76000 | 12909.09682 | −1159.486817 | 11749.61 |
| 77000 | 12946.17708 | −1196.567084 | 11749.61 |
| 78000 | 12982.77888 | −1233.168882 | 11749.61 |
| 79000 | 13018.9144 | −1269.304403 | 11749.61 |
| 80000 | 13054.59538 | −1304.985378 | 11749.61 |
| 81000 | 13089.8331 | −1340.323097 | 11749.61 |
| 82000 | 13124.63844 | −1375.028441 | 11749.61 |
| 83000 | 13159.02189 | −1409.411892 | 11749.61 |
| 84000 | 13192.99356 | −1443.383556 | 11749.61 |
| 85000 | 13226.56318 | −1476.953179 | 11749.61 |
| 86000 | 13259.74016 | −1510.130165 | 11749.61 |
| 87000 | 13292.53359 | −1542.923594 | 11749.61 |
| 88000 | 13324.95223 | −1575.342232 | 11749.61 |
| 89000 | 13357.00455 | −1607.394551 | 11749.61 |
| 90000 | 13388.69874 | −1639.088735 | 11749.61 |
| 91000 | 13420.0427 | −1670.432701 | 11749.61 |
| 92000 | 13451.0441 | −1701.434102 | 11749.61 |
| 93000 | 13481.71035 | −1732.100347 | 11749.61 |
| 94000 | 13512.0486 | −1762.438604 | 11749.61 |
| 95000 | 13542.06582 | −1792.455815 | 11749.61 |
| 96000 | 13571.7687 | −1822.158704 | 11749.61 |
| 97000 | 13601.16379 | −1851.553786 | 11749.61 |

TABLE 2-continued

The correction factors calculated by the regressive equation (Y = 2836.6 Ln(X) − 18970)

| the mean intensity of fluorescence obtained in 532 nm after microarraying | the mean intensity of fluorescence obtained in 532 nm after hybridization | correction factor | the mean normalized intensity of fluorescence obtained in 532 nm after hybridization |
|---|---|---|---|
| 98000 | 13630.25737 | −1880.647374 | 11749.61 |
| 99000 | 13659.06559 | −1909.445591 | 11749.61 |
| 100000 | 13687.56437 | −1937.954374 | 11749.61 |

INDUSTRIAL APPLICABILITY

As explained the above, final users can be provided a high-quality biological chip through introducing a process of quality examining for microarray of a biological material of the present invention to mass production process of a biological chip. In addition, bio-chip users of the present invention can further perform a step for measuring the intensity of light or heat emitted from hybridized microarray of biological material and a step for calculating a correction factor by using the above-measured intensity of light or heat to exclude error caused by discrepancy between size of each spots, in order to get more accurate experimental results.

What is claimed is:

1. A process for examining the quality of a microarray comprising a biological material, comprising:
   providing a substrate;
   providing a mixture of a probe and a light-emitting or heat-emitting compound that does not hybridize with the probe and can be removed by washing;
   spotting a predetermined amount of the mixture onto each of a plurality of distinct spots on the substrate to produce the microarray;
   measuring the amount of light or heat emitted from each spot of the plurality of distinct spots to generate numerical data for each spot;
   washing the microarray to remove the light-emitting or heat-emitting compound from each of the plurality of distinct spots; and
   for each spot of the plurality of distinct spots, calculating an arithmetic spotting mean of the amount of light or heat emitted from a spot after spotting based on the numerical data.

2. The process of claim 1, further comprising
   after removing, contacting the probe contained in each of the plurality of distinct spots with a target molecule comprising a sequence that is completely complementary to the sequence of the probe, wherein the target molecule is labeled with a heat-emitting or light-emitting compound such that upon hybridization of the target molecule with the probe, heat or light is emitted; and
   measuring the amount of heat or light emitted from each spot of the plurality of distinct spots to generate numerical hybridization data for each spot.

3. The process of claim 2, further comprising
   for each spot of the plurality of distinct spots, calculating an arithmetic hybridization mean of the amount of light or heat emitted from the spot after hybridization based on the numerical hybridization data.

4. The process of claim 3, further comprising
   calculating a regression equation from the arithmetic spotting mean for each spot and the arithmetic hybridization mean for each spot; and
   calculating a normalized arithmetic hybridization mean of heat or light emitted from each of the plurality of distinct spots from on the regression equation.

5. The process of claim 3, further comprising
   calculating a correction factor for each spot of the plurality of distinct spots, each spot having an arithmetic spotted mean corresponding to an amount of probe spotted, the correction factor comprising the difference between the calculated normalized mean and the arithmetic hybridized mean for an arithmetic spotted mean.

6. The process of claim 1, wherein the probe comprises one or more biological materials selected from the group consisting of a nucleic acid, a protein, a polysaccharide, and a phospholipid.

7. The process of claim 6, wherein the nucleic acid comprises a circular or a linear nucleic acid.

8. The process of claim 6, wherein the nucleic acid comprises DNA, cDNA, plasmid DNA, or RNA.

9. The process of claim 1, wherein the light-emitting or heat-emitting compound that does not hybridize with the probe is selected from the group consisting of a fluorescent material, a chemi-luminescent material, a bio-luminescent material, a calorimetric material, and a light-scattering material.

10. The process of claim 9, wherein the biological material is a nucleic acid and the light-emitting or heat-emitting compound is selected from the group consisting of fluorescein; coumarin; 4',5'-Dichloro-2',7'-dimethoxyfluorescein; tetramethylrhodamine; X-rhodamine; eosin; Oregon green; rhodamine green; rhodamine red; Texas red; and Rodamine.

11. The process of claim 9, wherein the biological material is a nucleic acid and the light-emitting or heat-emitting compound is 6-carboxyrhodamine 6G or 5-carboxyrhodamine 6G.

* * * * *